United States Patent [19]

Heullmann et al.

[11] Patent Number: 5,073,538
[45] Date of Patent: Dec. 17, 1991

[54] CYCLOALKYLIDENE DERIVATIVES AND FRAGRANCE COMPOSITION

[75] Inventors: Michael Heullmann, Heppenheim; Rainer Becker, Bad Duerkheim; Lothar Janitschke, Kleinniedesheim; Gerald Lauterbach, Bensheim; Wolfgang Barth, Wuppertal; Klaas Jansen, Ludwigshafen, all of Fed. Rep. of Germany

[73] Assignee: BASF Aktiengesellschaft, Ludwigshafen, Fed. Rep. of Germany

[21] Appl. No.: 571,899

[22] Filed: Aug. 24, 1990

[30] Foreign Application Priority Data

Aug. 26, 1989 [DE] Fed. Rep. of Germany ....... 3928242

[51] Int. Cl.$^5$ .................. A61K 7/46; C07D 311/96
[52] U.S. Cl. ........................ 512/9; 549/331
[58] Field of Search ............. 549/343, 331; 512/9

[56] References Cited

U.S. PATENT DOCUMENTS 4,010,286 3/1977 Hall et al. .
4,186,103 1/1980 Hall et al. .
4,192,782 3/1980 Hall et al. .
4,240,447 12/1980 Hall et al. .
4,652,402 3/1987 Brunke .

FOREIGN PATENT DOCUMENTS 2065172 10/1976 Fed. Rep. of Germany .
2006388 3/1979 Fed. Rep. of Germany .
1438100 6/1976 United Kingdom .

Primary Examiner—Nicky Chan
Attorney, Agent, or Firm—Oblon, Spivak, McClelland, Maier & Neustadt

[57] ABSTRACT

Cycloalkylidene derivatives of the general formulae Ia to Ic

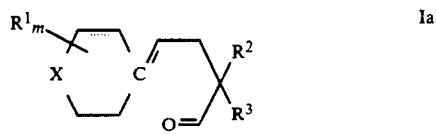

Ia

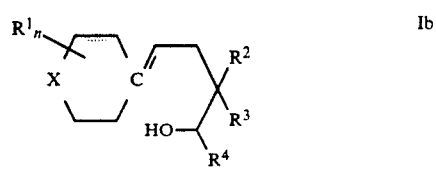

Ib

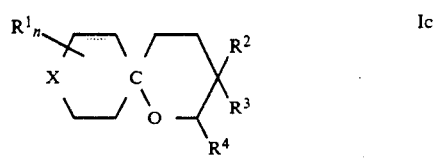

Ic where the dashed line is a possible additional chemical bond, the radicals $R^1$ are identical or different $C_1$–$C_4$-alkenyl groups, $R^2$ and $R^3$ are each methyl or ethyl, $R^4$ is hydrogen or one of the radicals $R^1$, X is oxygen, methylene or a chemical bond, m is from 0 to 3 or, when X is methylene, is from 1 to 3, or, when X is methylene and $R^1$ is methyl, is from 2 to 3 and n is from 0 to 3, are used as fragrance materials.

2 Claims, No Drawings

CYCLOALKYLIDENE DERIVATIVES AND FRAGRANCE COMPOSITION

The present invention relates to cycloalkylidene derivatives of the general formulae Ia to Ic

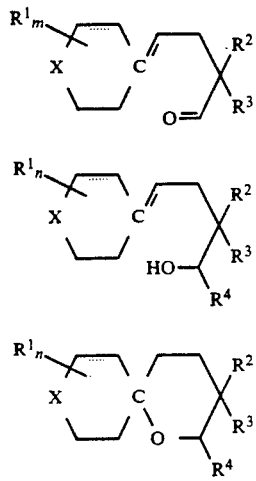

where the dashed line is a possible additional chemical bond, the radicals $R^1$ are identical or different $C_1$-$C_4$-alkyl or $C_2$-$C_4$-alkenyl groups, $R^2$ and $R^3$ are each methyl or ethyl, $R^4$ is hydrogen or one of the radicals $R^1$, X is oxygen, methylene or a chemical bond, m is from 0 to 3 or, when X is methylene, is from 1 to 3, or, when X is methylene and $R^1$ is methyl, is from 2 to 3 and n is from 0 to 3.

The present invention furthermore relates to processes for the preparation of the cycloalkylidene derivatives Ia to Ic and their use as fragance materials in cosmetic preparations and household and industrial care agents.

Cycloalkylidene derivatives of the type Ia having the structural unit of an unsubstituted cyclohexyl ring are known from the work of Cresson (Bull. Soc. Chim. France 10 (1964), 2618-2628). It has been found that the compound in which $R^2$ and $R^3$ are each methyl has a fresh, green, herbaceous note.

Spirocyclic ethers having the basic structure Ic have been disclosed as fragrance materials in U.S. Pat. Nos. 4,010,286, 4,186,103, 4,192,782 and 4,240,447; in contrast to Ic, in the said ethers $R^2$ and $R^3$ are each hydrogen and the ethers carry a methyl or methylene group in the 4-position of the dehydropyran ring.

It is an object of the present invention to provide novel compounds having novel fragance properties.

We have found that this object is achieved by the compounds Ia to Ic defined at the outset. We have furthermore found processes for their preparation, their use as fragrance materials and formulations of scent compositions which contain them.

Preferred compounds Ia are those in which X is a chemical bond or methylene and $R^1$ is an alkyl substituent in the 2- and 4- position.

Examples of such compounds are:
4-cyclopentylidene-2,2-dimethylbutanal,
4-[2,4,4'-trimethylcyclopentylidene]-2,2-dimethylbutanal,
4-[4-isopropylcyclohexylidene]-2,2-dimethylbutanal.

The compounds Ia are obtained by converting a cyclic ketone (II) with a vinylmagnesium halide into the vinylcarbinol (III), reacting III with phosgene or thionyl chloride in a conventional manner to give IV and reacting the latter with an aldehyde V:

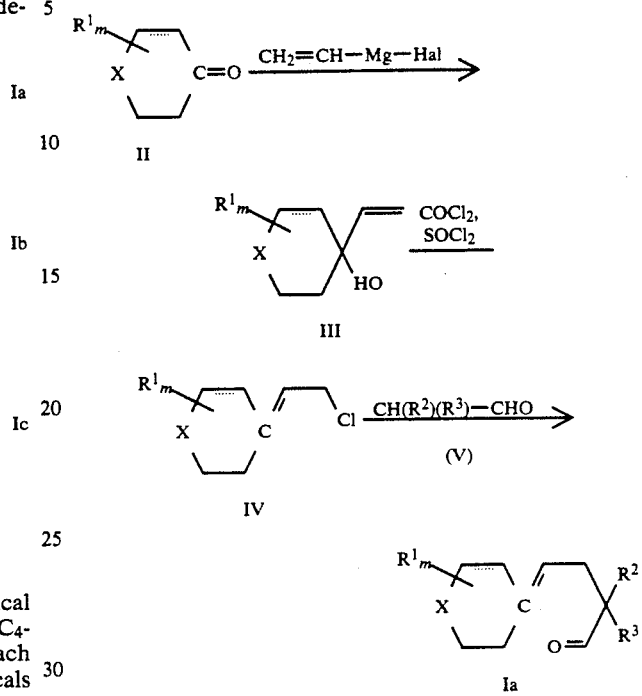

The reaction of cyclic ketones with a vinylmagnesium halide is known per se (Houben-Weyl, Methoden der organischen Chemie, Volume XIII/2a (1973), pages 47-527), so that detailed information in this respect is unnecessary.

The vinylcarbinols III can be converted into the compounds IV by reaction with a chlorinating reagent, preferably phosgene or thionyl chloride, at from $-80°$ to $150°$ C., preferably from $-20°$ to $20°$ C. The reactions can be carried out in the absence of a solvent or in a solvent. Suitable solvents are ethers, such as diethyl ether, esters, such as ethyl acetate, aliphatic and aromatic hydrocarbons, such as hexane or toluene, amides, such as dimethylformamide, sulfoxides, such as dimethy sulfoxide or mixtures of these solvents.

Finally, for the preparation of the cycloalkylidenealkanals, the allyl chlorides (IV) can be reacted with a 1-fold to 2-fold, preferably 1-fold to 1.5-fold, excess of aldehdye V. The reaction can advantageously be carried out in a basic medium, preferably in a two-phase system consisting of an aqueous alkali metal hydroxide solution and toluene, with the aid of a phase transfer catalyst. Suitable phase transfer catalysts are quaternary ammonium salts, such as tetrabutylammonium iodide.

Preferred compounds Ib are those having a cyclohexyl radical which carries either no radicals or identical or different radicals $R^1$ in the positions 2, 3, 4 or 6. Examples of such compounds are:
4-[cyclohexylidene]-2,2-dimethylbutanol,
4-[3,3-dimethylcyclohexylidene]-2,2-dimethylbutanol,
5-[2,5,6-trimethylcyclohex-2-enylidene]-3,3-dimethylpentan-2-ol,
4-[4-isopropylcyclohexylidene]-2,2-dimethylbutanol and 5-[4-isopropylcyclohexylidene]-3,3-dimethylpentan-2-ol.

The compounds Ib can be obtained by reducing the formyl group of the cycloalkylidenealkanals Ia, preferably with a complex metal hydride, such as lithium aluminum hydride or sodium borohydride, or by reaction with an alkyl- or vinylmagnesium halide.

The reduction with the metal hydrides can be carried out in an alcohol, such as methanol, ethanol or tert-butanol, at from 0° to 50° C., preferably 25° C. The reaction of the cycloalkylidenealkanals Ia with the Grignard compounds is effected by methods generally known from the literature, so that further information in this respect is unnecessary (Houben-Weyl, Methoden der Organischen Chemie, Volume XIII/2a (1973), pages 47-527).

Those spirocyclic ethers (Ic) which are composed of two six-membered rings and carry one of the radicals $R^1$ in the 7- or 8-position show the most interesting fragrance notes. Examples of such compounds are:
3,3'-dimethyl-8-isopropyl-1-oxaspiro[5.5]undecane,
3,3'-dimethyl-7,7'-dimethyl-1-oxaspiro[5.5]undecane,
2-methyl-3,3'-dimethyl-7,7'-dimethyl-1-oxaspiro[5.5]undecane,
2-vinyl-3,3'-dimethyl-7,7'-dimethyl-1-oxaspiro[5.5]undecane,
2-methyl-3,3'-dimethyl-7,7'-dimethyl-1-oxaspiro[5.5]undecane.

The compounds Ic are preferably obtained by cyclization of the corresponding cycloalkylidenealkanols Ib in the presence of acidic catalysts.

The reaction can be carried out at from −80° to 100° C., preferably from −20° to 50° C., in the absence of a solvent or in an inert solvent. Suitable solvents are hydrocarbons, such as toluene, chlorohydrocarbons, such as methylene chloride and chlorobenzene, and ethers, such as tetrahydrofuran and methyl tert-butyl ether. Suitable acidic catalysts are inorganic and organic acids, such as sulfuric acid, phosphoric acid, hydrochloric acid, acetic acid, oxalic acid and p-toluenesulfonic acid, acidic ion exchangers and Lewis acids, such as zinc chloride and boron trifluoride.

The novel compounds Ia and Ib have fresh and floral notes, whereas the spirocyclic ethers have a pronounced sensual fragrance. They are used alone or preferably with other fragrance materials in the conventional combinations for the preparation of perfumes, for perfuming, i.e. for imparting fragrance properties to, or improving or modifying the fragrance properties of, cosmetic products and detergent compositions for household and industrial use.

EXAMPLES 1 TO 6

Preparation of the Compounds Ia

A solution of 4.5 mol of vinylmagnesium chloride in 3 l of tetrahydrofuran was added to 3.5 mol of a cyclic ketone (II) at 25° C. in the course of 2 hours. After the mixture had been stirred for 12 hours, the Grignard compound was hydrolyzed with 450 ml of water, after which the mixture was extracted with methyl tertbutyl ether. Working up in the conventional manner gave the vinylcarbinol III.

2.2 mol of phosgene were passed into 2.0 mol of the vinylcarbinol (III), dissolved in a mixture of 600 ml of toluene and 180 ml of dimethylformamide, at 0° C. in the course of 4 hours. The reaction mixture was then stirred for a further hour. For working up, the mixture was washed thoroughly with twice 1 l of water and neutralized with NaHCO$_3$ solution and the organic phase was evaporated down. This solution was used directly in the subsequent reaction.

2.2 mol of isobutyraldehyde (V) and 1.65 mol of allyl chloride IV, dissolved in 600 ml of toluene/dimethylformamide, were added dropwise to a solution of 27 mmol of tetrabutylammonium iodide in 25% strength sodium hydroxide solution at 50° C. Stirring was then carried out for 16 hours at 50° C. and for 4 hours at 70° C. For working up, the organic phase was separated off, washed with cold water, dried with magnesium sulfate and evaporated down, after which the residue was distilled over a Vigreux column.

The details of these experiments and their results are shown in Table 1.

TABLE 1

Preparation of the compounds Ia

| X | $R^1$ | | III Yield bp. | IV Yield bp. | Ia Yield bp. | Fragrance note |
|---|---|---|---|---|---|---|
| 1 chem. bond | H | Single bond | 65% 36°/0.4 mm | 58% Crude product | 53% 60°/0.4 mm | Fruity |
| 2 CH$_2$ | 2,3,6-CH$_3$ | Single bond | 57% 64°/0.4 mm | 46% 60°/0.2 mm | 46% 136° C./0.45 mm | Burnt Spicy |
| 3 CH$_2$ | 4-CH(CH$_3$)$_2$ | Single bond | 77% 123°/38 mm | 82% Crude product | 56% 76°/0.3 mm | Floral |
| 4 CH$_2$ | 4-CH(CH$_3$)$_2$ | Double bond | 90% 73°/0.5 mm | 43% 85°/0.4 mm | 51% 142°/0.4 mm | Floral |
| 5 CH$_2$ | 3,3-CH$_3$ | Single bond | 73% 60°/0.4 mm | 55% 53° 0.3 mm | — | — |
| 6 — | 2,4,4-CH$_3$ | Single bond | — | 25% Crude product | 56% 95°/0.15 mm | Rose Greenish |

The crude products were further reacted as a solution in toluene, without purification.

EXAMPLES 7 TO 14

1 mol of cyclohexylidenealkanal (Ia) was added dropwise to a solution of 0.63 mol of sodium borohydride in 1.2 l of ethanol at 25° C. in the course of 2 hours. The reaction mixture was then stirred for a further 12 hours at 25° C. For working up, the reaction solution was evaporated down, the residue was taken up in methyl tertbutyl ether and 10% strength H$_2$SO$_4$ was added. The organic phase was separated off, neutralized with sodium bicarbonate solution, dried over magnesium sulfate and evaporated down, and the residue was distilled.

The alcohols listed in the Table below were prepared either similarly or by reaction with a corresponding Grignard compound.

TABLE 2

Preparation of the compounds Ib

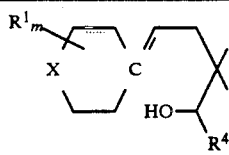

| X | R$^1$ | R$^4$ | Yield | bp. | Fragrance note |
|---|---|---|---|---|---|
| 7 CH$_2$ | — | H | 63% | 79° C./0.2 mm | Fruity, rose |
| 8 — | — | H | 76% | 70° C./0.15 mm | Fruity |
| 9 CH$_2$ | 2,3,6-CH$_3$ | H | 79% | 111° C./0.15 mm | Metallic, chemical |
| 10 — | 2,4,4'-CH$_3$ | H | 68% | 81° C./0.2 mm | Woody, faecal |
| 11 — | 2,4,4'-CH$_3$ | CH$_3$ | 74% | 94° C./0.18 mm | Aldehydic, green |
| 12 — | — | CH$_3$ | 75% | 82° C./0.18 mm | Fatty, floral |
| 13 CH$_2$ | 4-CH(CH$_3$)$_2$ | H | 76% | 100° C./0.3 mm | Fruity, floral |
| 14 CH$_2$ | 4-CH(CH$_3$)$_2$ | CH$_3$ | 67% | 120° C./0.3 mm | Woody, spicy |

EXAMPLES 15 TO 19

60 mmol of cyclohexylidenealkanol (Ib) were added dropwise to 7.5 ml of boron trifluoride etherate in 45 ml of methylene chloride at 0° C. The reaction solution was stirred for 2 hours, poured onto ice water and then extracted with methylene chloride. Working up in the conventional manner gave the spirocyclic ethers Ic.

The details of these experiments and their results are shown in Table 3.

We claim:
1. A cycloalkylidene derivative of the formula Ic

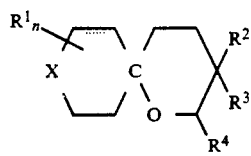

where the dashed line is an optional additional chemical bond, the radicals R$^1$ are identical or different C$_1$-C$_4$-alkyl or C$_2$-C$_4$-alkenyl groups, R$^2$ and R$^3$ are each methyl or ethyl, R$^4$ is hydrogen or one of the radicals R$^1$, X is methylene or a chemical bond, and n is from 0 to 3.

2. A fragrance composition which contains a cycloalkylidene derivative of the formula Ic as claimed in claim 1.

* * * * *

TABLE 3

Preparation of the compounds Ic

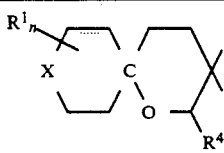

| | | | | | Fragrance note | |
| X | R$^1$ | R$^4$ | Yield | bp. | 100% | 10%[1] |
|---|---|---|---|---|---|---|
| 15 CH$_2$ | — | H | 75% | | | — |
| 16 CH$_2$ | 7,7-CH$_3$ | H | 80% | | Faecal, leather-like | Leather-like |
| 17 CH$_2$ | 7,7-CH$_3$ | CH$_3$ | 80% | | Faecal, herbaceous | Herbaceous |
| 18 CH$_2$ | 7,7-CH$_3$ | —CH=CH$_2$ | 78% | | Faecal, sage | Sage |
| 19 CH$_2$ | 8-CH(CH$_3$)$_2$ | H | 75% | | Civet | Civet |

[1] 10% strength solution in ethyl alcohol